(12) United States Patent
Petersen et al.

(10) Patent No.: US 7,813,609 B2
(45) Date of Patent: Oct. 12, 2010

(54) IMAGING CATHETER WITH INTEGRATED REFERENCE REFLECTOR

(75) Inventors: Christopher Petersen, Carlisle, MA (US); Stephen M. McCartin, Chelmsford, MA (US); Joseph M. Schmitt, Andover, MA (US); Joel M. Friedman, Andover, MA (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 11/983,526

(22) Filed: Nov. 12, 2007

(65) Prior Publication Data

US 2009/0122320 A1    May 14, 2009

(51) Int. Cl.
    *G02B 6/06* (2006.01)
(52) U.S. Cl. ................................. 385/117; 385/116
(58) Field of Classification Search .......... 385/116–117
    See application file for complete search history.

(56) References Cited

U.S. PATENT DOCUMENTS

| 4,548,473 | A | 10/1985 | Lo et al. |
|---|---|---|---|
| 5,321,501 | A | 6/1994 | Swanson et al. |
| 5,459,570 | A | 10/1995 | Swanson et al. |
| 5,465,147 | A | 11/1995 | Swanson |
| 5,518,810 | A | 5/1996 | Nishihara et al. |
| 5,632,767 | A | 5/1997 | Sinofsky |
| 5,643,253 | A | 7/1997 | Baxter et al. |
| 5,748,598 | A | 5/1998 | Swanson |
| 5,784,352 | A | 7/1998 | Swanson et al. |
| 5,908,415 | A | 6/1999 | Sinofsky |
| 5,947,959 | A | 9/1999 | Sinofsky |
| 5,956,355 | A | 9/1999 | Swanson et al. |
| 6,111,645 | A | 8/2000 | Tearney et al. |
| 6,134,003 | A | 10/2000 | Tearney et al. |
| 6,160,826 | A | 12/2000 | Swanson et al. |
| 6,191,862 | B1 | 2/2001 | Swanson et al. |
| 6,270,492 | B1 | 8/2001 | Sinofsky |
| 6,282,011 | B1 | 8/2001 | Tearney et al. |
| 6,348,960 | B1 | 2/2002 | Etori et al. |
| 6,421,164 | B2 | 7/2002 | Tearnet et al. |
| 6,445,939 | B1 | 9/2002 | Swanson et al. |
| 6,485,413 | B1 | 11/2002 | Boppart et al. |

(Continued)

FOREIGN PATENT DOCUMENTS

JP          63-127201           5/1988

OTHER PUBLICATIONS

Annex to Form PCT/ISA206 Communication Relating to the Results of the Partial International Search for International application No. PCT/US2008/012701, mailed on Feb. 27, 2009.

(Continued)

*Primary Examiner*—Charlie Peng
*Assistant Examiner*—Eric Wong
(74) *Attorney, Agent, or Firm*—K&L Gates LLP (57) ABSTRACT

In part, the invention relates to a lens assembly. The lens assembly includes a micro-lens; a beam director in optical communication with the micro-lens; and a substantially transparent film. The substantially transparent film is capable of bi-directionally transmitting light, and generating a controlled amount of backscatter. In addition, the film surrounds a portion of the beam director.

19 Claims, 13 Drawing Sheets

U.S. PATENT DOCUMENTS

| | | | |
|---|---|---|---|
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,879,851 B2 | 4/2005 | McNamara et al. | |
| 6,891,984 B2 | 5/2005 | Petersen et al. | |
| 6,974,557 B1* | 12/2005 | Webler et al. | 264/443 |
| 7,241,286 B2 | 7/2007 | Atlas | |
| 7,408,648 B2 | 8/2008 | Kleen et al. | |
| 2003/0091814 A1 | 5/2003 | Benz et al. | |
| 2003/0118302 A1* | 6/2003 | James et al. | 385/117 |
| 2003/0216720 A1 | 11/2003 | Sinofsky | |
| 2004/0059397 A1 | 3/2004 | Sinofsky et al. | |
| 2004/0215166 A1 | 10/2004 | Atlas | |
| 2005/0128479 A1 | 6/2005 | Gilbert et al. | |
| 2005/0201662 A1 | 9/2005 | Petersen et al. | |
| 2006/0095065 A1 | 5/2006 | Tanimura et al. | |
| 2006/0241503 A1 | 10/2006 | Schmitt et al. | |
| 2006/0274313 A1 | 12/2006 | Gilbert et al. | |
| 2007/0015969 A1* | 1/2007 | Feldman et al. | 600/160 |
| 2007/0260198 A1 | 11/2007 | Atlas | |
| 2008/0015560 A1* | 1/2008 | Gowda et al. | 606/15 |
| 2008/0030865 A1 | 2/2008 | Gilbert et al. | |
| 2008/0161696 A1 | 7/2008 | Schmitt et al. | |
| 2008/0165366 A1 | 7/2008 | Schmitt et al. | |
| 2008/0180666 A1 | 7/2008 | Gilbert et al. | |

OTHER PUBLICATIONS

PCT International Preliminary Report on Patentability for International Application No. PCT/US2008/12701, issued May 18, 2010.

Written Opinion of the International Searching Authority, International application No. PCT/US2008/012701, mailed on May 14, 2009.

International Search Report, International application No. PCT/US2008/012701, mailed on May 14, 2009.

* cited by examiner

IMAGING CATHETER WITH INTEGRATED REFERENCE REFLECTOR

FIELD OF INVENTION

This invention relates to optical imaging, and more specifically to the design of fiber optic probes for optical coherence tomography (OCT) and related imaging techniques.

BACKGROUND

Optical interference is a phenomena used widely throughout the sciences. In particular, the use of short-coherence (or 'low-coherence') interferometric imaging has become an important imaging modality in several fields and notably in medical applications. In interferometric imaging, light from a known and controlled optical path (the 'reference path') is caused to interfere with light returned from an unknown path such that information about this unknown path (the 'sample path') may be determined by an analysis of the resulting interferogram.

In short-coherence imaging, the interferogram contains the depth location information of structures within the sample being analyzed. Scanning short-coherence light over a sample volume to produce tomographic images is known as Optical Coherence Tomography, or OCT. In recent years, practical laser-based light sources with coherence lengths of 20 μm or less have become available, promoting the use of OCT in several fields including ophthalmology, general microscopy, cardiology and oncology.

A particular advantage of OCT is its inherent compatibility with fiber optics making it a nearly ideal imaging modality for non-invasive or minimally invasive medical procedures.

Central to all OCT implementations is the requirement that the lengths of the sample and reference paths be matched to ensure the interference effect being recorded corresponds to a desired scan region within the sample. In the case of relatively long optical catheters required in many procedures (approximately 1.5 to 2 meters is common) this requirement for matching the path lengths may become difficult to achieve, especially when many practical implementations of OCT require matching on the millimeter scale. Furthermore, the very thin fibers used in these catheters can easily stretch or contract several millimeters during use.

When using OCT in any application, the optical 'zero-point' is critical. This defines where, in the image space, the so-called reference plane exists. By convention, surface planes are in the x-y plane, and the depth occurs along the z-axis. In a microscope application for example, it may be beneficial to set the zero point at the surface of the microscope slide, so specimens can be measured against this known surface. In a catheter inserted into a bodily lumen, the most useful reference plane is the outer surface of the catheter tip itself, and all distances are measured outward from this location.

For a rotating catheter, the x-y-z space is best represented in polar coordinates (angle and radial distance). Hence the z-axis becomes the radial distance from the center. Practically, setting a match point means that the optical length from the chosen reference plane in the sample is equal to the primary optical length in the reference arm. The high speed changing of the reference arm length in scanning represents only a small variation on the primary length. Because OCT penetrates tissue only a few millimeters, the scan is practically limited to typically 1-5 mm, whereas the actual lengths of the sample and reference arms may be several meters.

For example, in the case of optical catheters used in cardiology, the instrument itself will be located outside the nominal 'sterile field' surrounding the patient, the catheter itself will be inside this field, and an umbilical will be used to join the two. The total optical length of the sample arm (catheter plus umbilical) can easily approach 5 meters, which will also be the primary length of the reference arm. Since scanning will be perhaps 5 mm, this represents 0.1% of the total length. Measurement accuracy is required to be 0.1 mm or better in this application. Since it is not cost-effective to control the lengths of each optical fiber within the catheter and umbilical to sub-millimeter dimensions, most design approaches use an adjustable reference path within the optical imaging equipment to adjust to each catheter as it is used.

However, a medical application may use many disposable catheters per day; all interfaced to the same imaging equipment. Thus, while the primary path length adjustment can work quite effectively, it usually requires an initial adjustment by a skilled operator who understands the optical reflection pattern or 'signature' of the catheters that will be recorded by OCT to determine how to adjust the reference path to coincide with the outer surface of the catheter tip. Again, the adjustment of the image zero-point, or reference plane location is performed by adjusting the primary path-length of the reference arm. This adjustment is often termed 'z-offset' of the reference arm and is controlled via a motor, called simply the z-offset motor. By convention, the instrument z-offset is zero when the sample arm length (catheter) is manufactured exactly as designed; is negative when the catheter is too short; and positive when the catheter is too long.

These optical catheters typically have a lens and reflector structure placed at their distal tip to focus and direct the light for scanning purposes. The light typically propagates through one or more transparent sheaths that comprise the catheter outer structure. Each of the interfaces can and will cause a reflection that will be detected by OCT. Hence, it may be challenging to determine which of those reflections corresponds to the desired optical reference point ('zero-point') of the system. Since measurements are made based on this zero-point setting, setting it correctly can have significant importance in medical applications. Furthermore, because there may be several closely spaced and similar intensity reflections, the use of software to detect the proper zero-offset ('z-offset') is extremely problematic and unreliable.

As noted, the optical fiber can stretch significantly on these scales when the catheter is advanced or retracted. For example, using the known yield strength of standard optical fibers used in OCT, and the catheter length, it is easy to show that 10 mm of stretch can occur before the fiber breaks. Typical forces encountered in real situations will only cause a 1 mm stretch or less, but many medical measurements require accuracy of ¼ millimeter or better.

a simple, cost effective method for reliably determining the optical match point ('zero-point') of the catheter is needed. Furthermore, this method should be compatible with real-time video rate imaging so that the zero-point can be tracked as the catheter is maneuvered, retracted or advanced. The present invention addresses these issues.

SUMMARY OF THE INVENTION

In one aspect, the invention relates to fiber optic imaging probe having an elongated section and a proximal and a distal end, the probe comprising a thin controlled optical scattering material applied to the distal end.

In another aspect, the invention relates to an optical element. The optical element includes a membrane having a first surface and a second surface. The membrane includes a polymer and at least one back-scattering element for controlled optical back-scattering disposed therein. Further, the membrane allows transmission of substantially undistorted imaging light.

The aspects of the invention described herein can include further embodiments. For example, the optical element can further include a plurality of back-scattering elements wherein the at least one back-scattering element and each of the plurality of back-scattering elements is a particle having a particle dimension, the plurality of back-scattering elements disposed within the polymer. In one embodiment, the membrane is shaped to form a curved surface suitable for engulfing, surrounding, enveloping or otherwise covering an optical fiber endface or micro-lens.

The particle dimension, in some preferred embodiments, is less than about 1.5 μm. Further, the particles can include titanium, zinc, aluminum, and/or other materials suitable for scattering light. The plurality of scattering elements can have a concentration of about 0.1% doping concentration by volume. The optical element can further include an elongate member, wherein the membrane is shaped to form a sheath within which the elongate member is disposed to form a portion of a probe tip.

In another aspect, the invention relates to an imaging probe. The probe includes an elongate section having a first end and a second end; the second end forming a probe tip capable of intra-lumen imaging, the probe tip comprising a scattering material, the elongate section adapted to transmit light reflected by the scattering material to the first end of the elongate section.

In one embodiment, the elongate section is an optical fiber. The elongate section can be a sheath. Also, the probe can further include an optical fiber disposed within the sheath. The scattering material can include a plurality of light scattering particles dispersed in a matrix. The scattering particles can include titanium and/or other materials known to scatter light. Also, the matrix can include polyethylene terepthalate and/or other polymers.

In another aspect, the invention relates to a lens assembly. The lens assembly includes a micro-lens; a beam director in optical communication with the micro-lens; and a substantially transparent film. The substantially transparent film is capable of bi-directionally transmitting light, and generating a controlled amount of backscatter. In addition, the film surrounds a portion of the beam director.

In one embodiment of an aspect of the invention, the controlled amount of backscatter is in an amount of light at least sufficient to generate a reference point in an imaging system for calibration of at least one imaging system parameter. The substantially transparent film can also include a plurality of scattering particles. The micro-lens can be in optical communication with an optical fiber. Further, the substantially transparent film can be shaped to form an imaging probe tip. Also, the probe tip can be used for optical coherence tomography imaging.

In still another aspect, the invention relates to a method of calibrating an optical coherence tomography system. The method includes generating scan data in response to light reflected from a sample, the reflected light passing through a bi-directional substantially transparent optical element; generating reference data in response to scattered light reflected from a scattering element disposed within the bi-directional substantially transparent optical element; and calibrating the optical coherence tomography system to determine the relative position of subsequent scans in response to the reference data.

In one embodiment of an aspect of the invention, scan data includes a set of angles and a set of radial distances. Further, the reference data can include a set of angles and a set of radial distances. The step of calibrating can include searching for a ring pattern within the reference data.

In yet another aspect, the invention relates to a method of fabricating an optical element. The method includes selecting a membrane material suitable for intra-lumen use in an animal; selecting a dopant suitable for dispersion in the membrane material, the dopant adapted to scatter light in response to an optical source; determining a dopant volume concentration such that a radial scan of a doped membrane generates a defined pattern; doping the membrane with the selected dopant to substantially obtain the determined dopant volume concentration; and shaping the membrane for intra-lumen use in an animal.

In on embodiment, the membrane includes polyethylene terepthalate. The dopant volume concentration can include about 0.1% doping concentration by volume. The selected dopants can include an oxide. Further, the defined pattern can be selected from the group consisting of a ring and a spiral.

DETAILED DESCRIPTION OF THE PREFERRED EMBODIMENT

Figure 1:
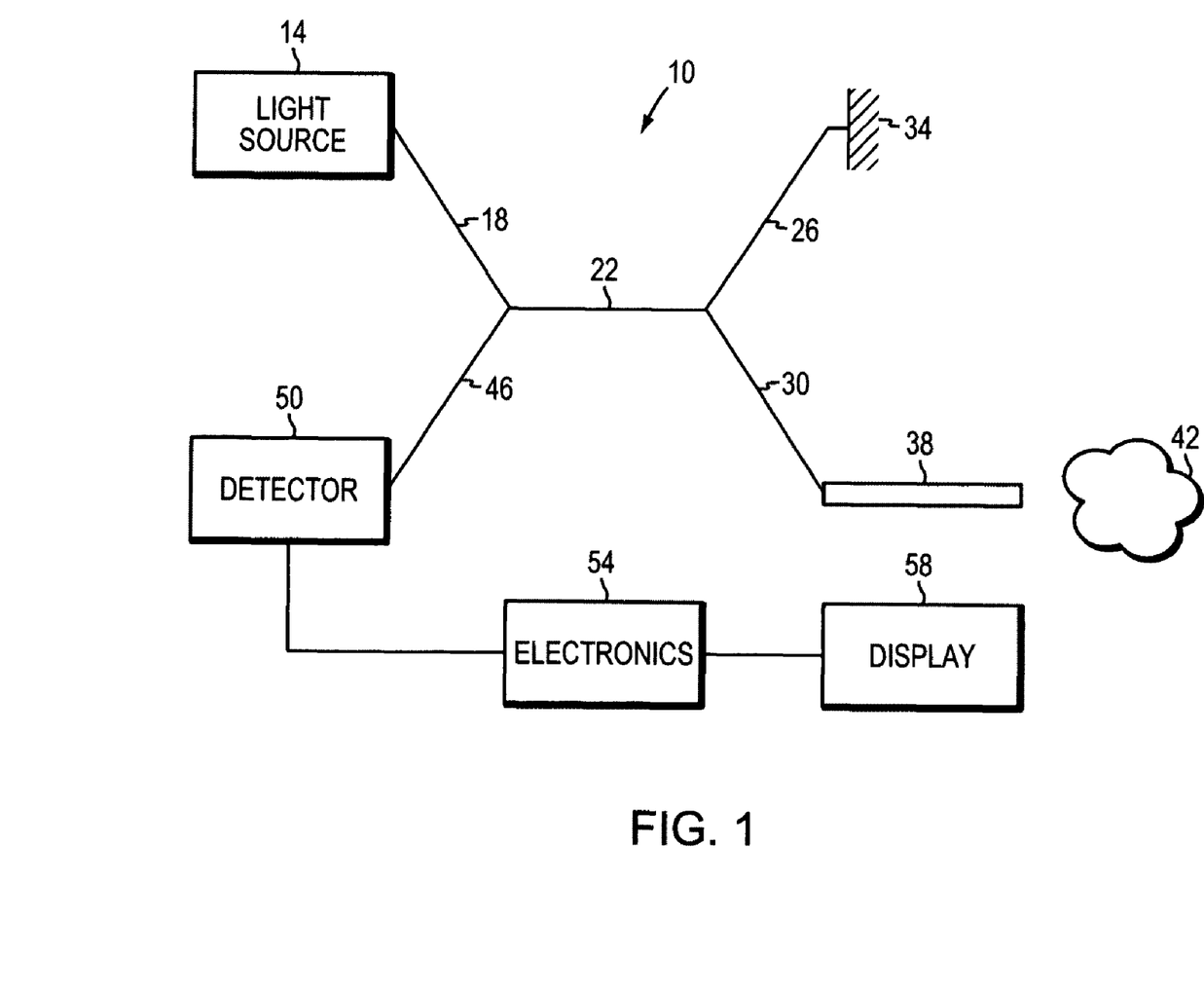
FIG. 1 is a block diagram of an OCT system suitable for use with the optical probe of the invention.

In brief overview and referring to FIG. 1, a generalized OCT interferometer 10 is shown which is suitable for use with the catheter imaging system of the invention. A light source 14, such as a diode laser, produces short-coherence length light that passes by way of an optical fiber 18 into an optical fiber coupler 22. Light entering the coupler 22 is the split along two optical fiber paths 26 and 30. One path 26 terminates at a movable reflector 34, while the other enters a probe 38 and is emitted toward an object of interest 42.

Light reflected by the movable reflector 34 passes back along optical fiber 26 to the coupler 22. Similarly light reflected by the object of interest 42 passes back along optical fiber 30 to the coupler 22 and combines with the light reflected by the movable reflector 34 to form an interference pattern. This combined light passes through optical fiber 46 and is detected by a detector 50. The output signal from the detector 50 is processed by electronics 54 and an image formed on display 58.

Figure 2:
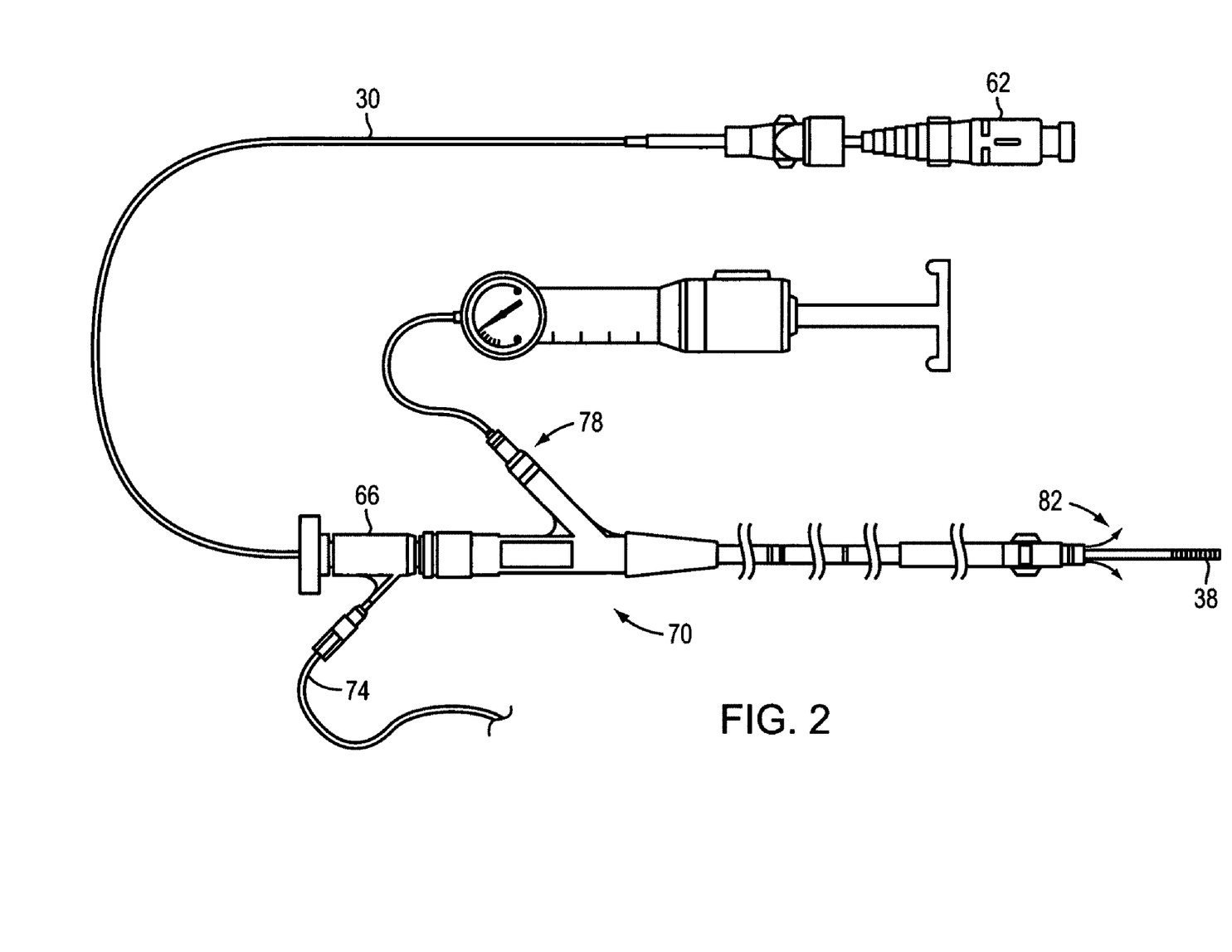
FIG. 2 is a schematic diagram of an optical catheter system, suitable for use with OCT imaging in coronary arteries.

An example of an imaging catheter suitable for use as the probe in FIG. 1 is shown in FIG. 2. In this embodiment, the imaging probe 38 is the tip of a coronary vessel imaging catheter. A connector 62 attaches to the optical coupler 22 of the system of FIG. 1. The optical fiber 30 enters a y-body connector 66 attached to a balloon catheter 70. This catheter 70 includes a flushing port 74 and a balloon inflation port 78 as well as a flush exit 82.

Figure 3:
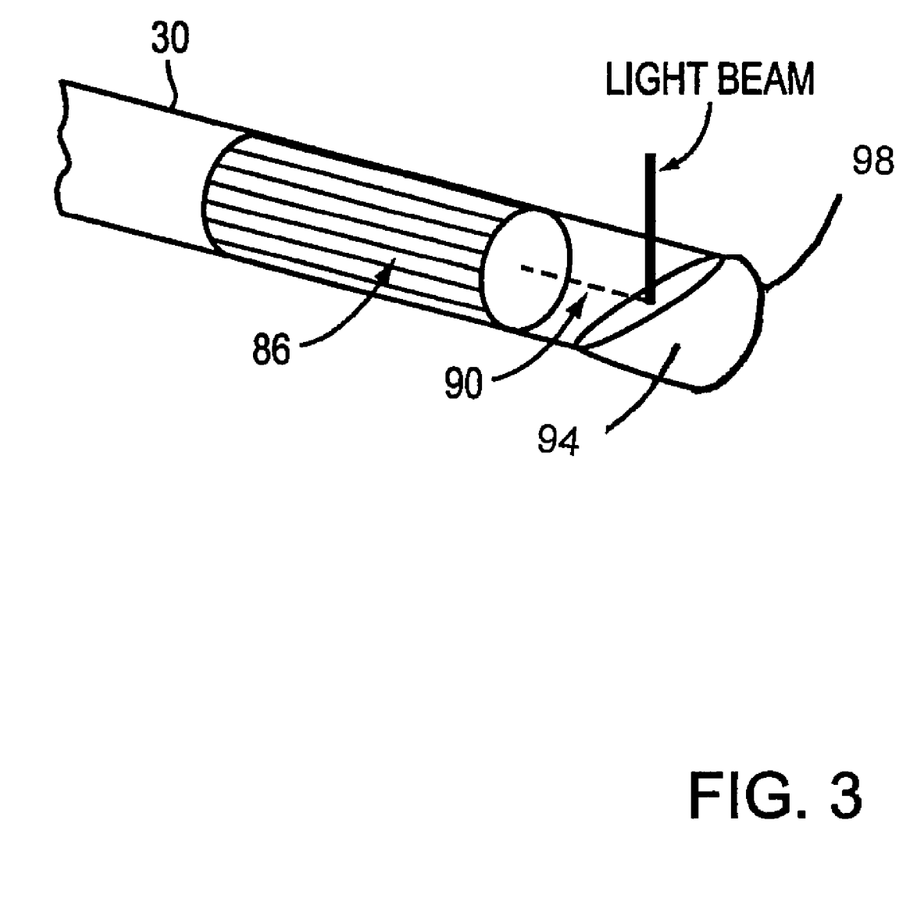
FIG. 3 is a schematic diagram of the optical fiber tip, with micro lens and protective cover.

FIG. 3 depicts an embodiment of the image wire tip of the probe 38. The optical fiber 30 terminates in a micro-lens assembly 86 which focuses the light at a distance from the micro-lens assembly 86. Light emitted from the micro-lens assembly 86 is reflected by a beam deflector 90 so to as to pass at substantially right angles to the optical axis of the fiber 30. The entire fiber assembly is covered by a protective transparent sheath 94 sealed at one end 98 as discussed below.

Figure 3A:
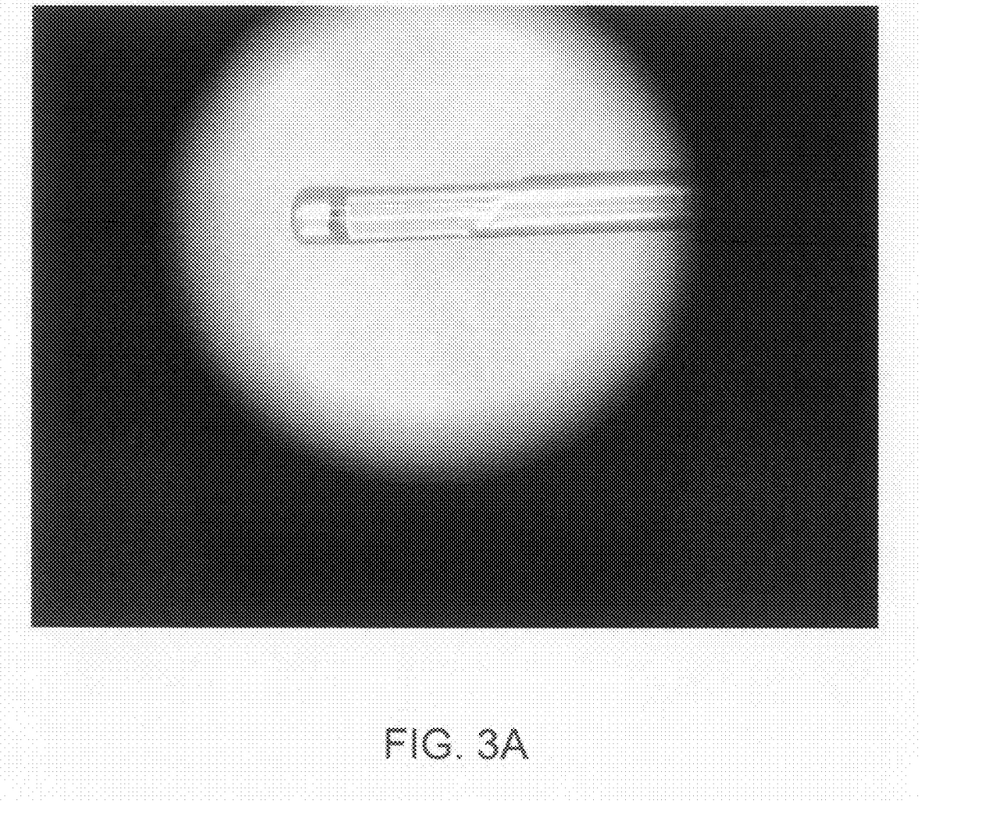
FIG. 3a is a photomicrograph of an embodiment of the probe shown schematically in FIG. 3.

As explained in U.S. Pat. No. 6,891,894, herein incorporated by reference, a particularly advantageous fiber lens design uses total internal reflection from a silica-air interface to provide the needed radial scan inside a lumen, such as an artery, by simply rotating the fiber. Since the total internal reflection depends on the refractive index mismatch between the silica and air, direct immersion in a fluid will eliminate this reflection and the light will propagate forward instead, destroying the ability to take useful radial scan. As shown in the '894 patent and in FIGS. 3 and 3a, the air-silica interface can be preserved by using a clear protective cover 94 adhered directly to the fiber lens assembly. Such a cover can be made preferably from a heat-shrinkable material such as polyester (Polyethylene Terepthalate, or PET). PET is widely used in industry and medical devices and has good biomedical compatibility properties.

Such a PET cover has inherent low back-reflection, so in its usual format it is unsuitable for the purpose of providing a fixed reference reflection. However, with care, dopants can be added to the raw PET material (before the tube shape is formed) increasing the native back-reflection.

Several materials exist as a suitable dopant. In particular titanium dioxide ($TiO_2$) is advantageous. $TiO_2$ is used in many paint formulations due to its excellent light scattering properties. Further it is inert and can be made in bulk. The particle size can be made much smaller than the optical wavelengths of interest (nominally 1.3 μm), making the scattering 'Rayleigh' in nature. Thus the outgoing and returning light wavefronts are not appreciably disturbed, thereby minimizing any potential image degradation at sufficiently low concentrations of dopant.

A key step in the creation of the material is uniformly mixing $TiO_2$ particles in the raw PET such that, when drawing the PET into tubing, the correct concentration is realized with high uniformity. In addition, because OCT imaging has tremendous sensitivity and large dynamic range (typically 100 dB of sensitivity and >60 dB of dynamic range can be achieved in practical instruments) care must be used to calculate then achieve the optimal doping level of $TiO_2$ in the material.

Basic scattering theory can be used to arrive at a doping concentration in the material. In a typical OCT image in the coronary arteries, the minimum noise in the instrument is about −100 dB. That is, about 1 ten-billionth of the optical output power applied to the object of interest and a typical image has approximately 40 dB of useful dynamic range. The image processing electronics and software are optimized for this range, so the probe reflector element should be optimized to be near the maximum detectable peak of the image intensity, which is about −60 dB (−100+40). This means that the probe reflector should be the brightest object in the image.

As described herein the probe reflector element can include, but is not limited to, a membrane, a film, a cap, a cover, or other material. In some embodiments, the reflector element is flexible or inflexible. The reflector element can be shaped in various geometries, such that portions of the reflector are curved, planar, or substantially planar.

Basic scattering theory for particles and classic radar cross-section theory estimates that the fraction of light reflected from a single $TiO_2$ particle is given by the expression:

$$L_R = \frac{\sigma_b}{V_i} l_c \Delta\Omega$$

where $L_R$ is the return light fraction, $\sigma_b$ is the scattering cross-section (calculated from standard MIE theory), $V_i$ is the volume of the particle, $l_c$ is the interaction length (from Radar theory), in this case the coherence length of the OCT light, and $\Delta\Omega$ is acceptance angle (solid angle) of the micro-lens. Thus, for a particle size of roughly 45 nm with a scattering cross section of approximately $4.26 \times 10^{-7}$ μm$^2$, and light having a coherence length of about 15 μm irradiating the particle through a micro-lens having a solid angle of ~0.004, the reflected light fraction, $L_R$, is about 0.006, or −32 dB.

Therefore the total light returned from the probe reference reflector element material should be equal to the single particle light fraction times the volume fraction (doping concentration). Because this should be equal to about −60 dB (from above), a reduction of −30 dB (or 0.001) is required. Therefore, the volume fraction should be about 0.001, or about 0.1% doping concentration by volume. This should result in a strong, but not overpowering reference reflection by the $TiO_2$ particles.

Figure 4A:
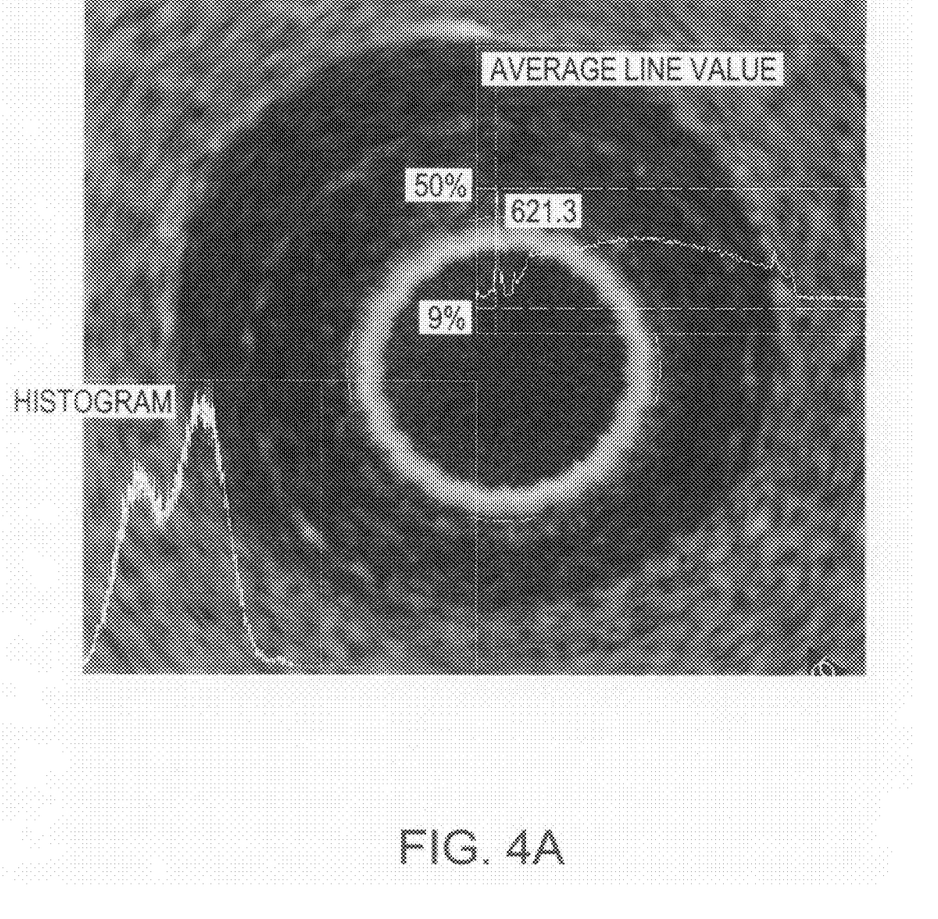
FIGS. 4a and 4b depict an image taken with a doped plastic lens cover and an undoped plastic (such as PET) cover, respectively.
Figure 4B:
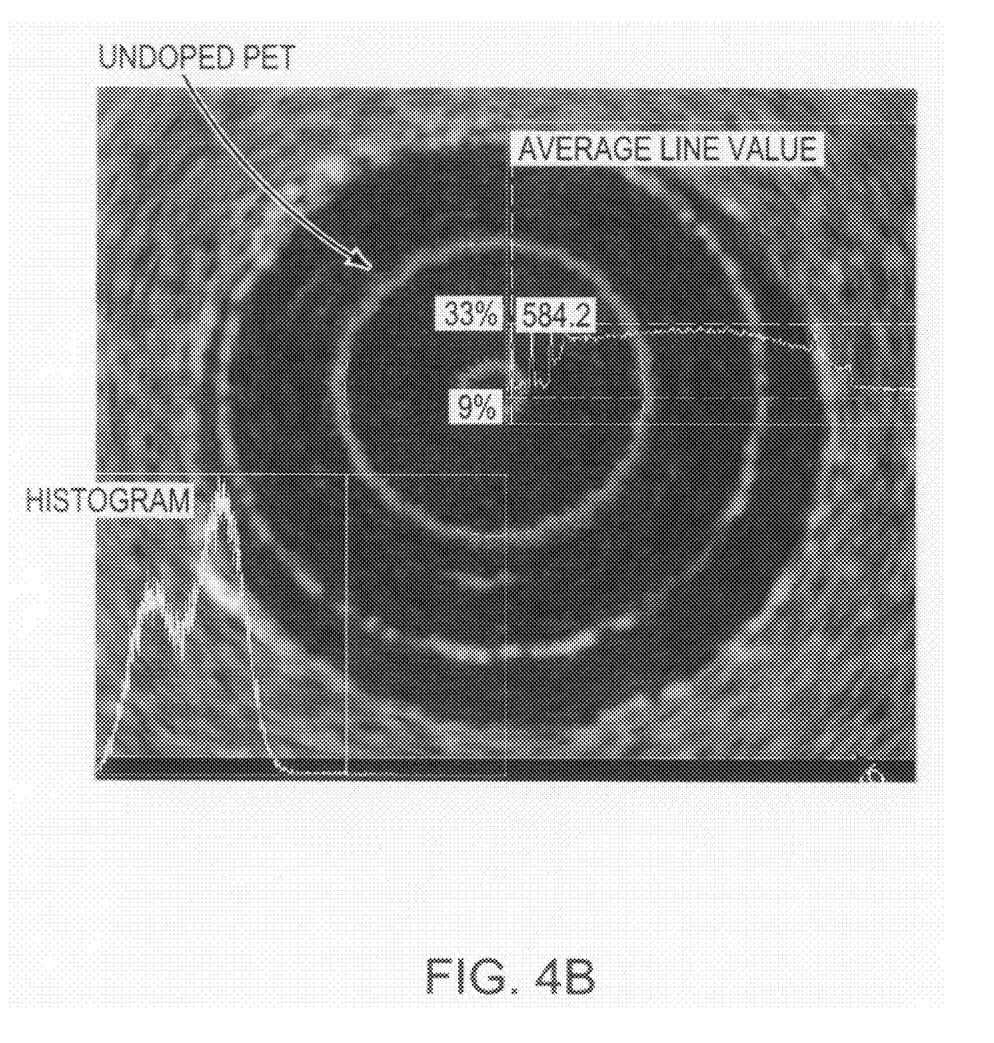
Figure 4C:
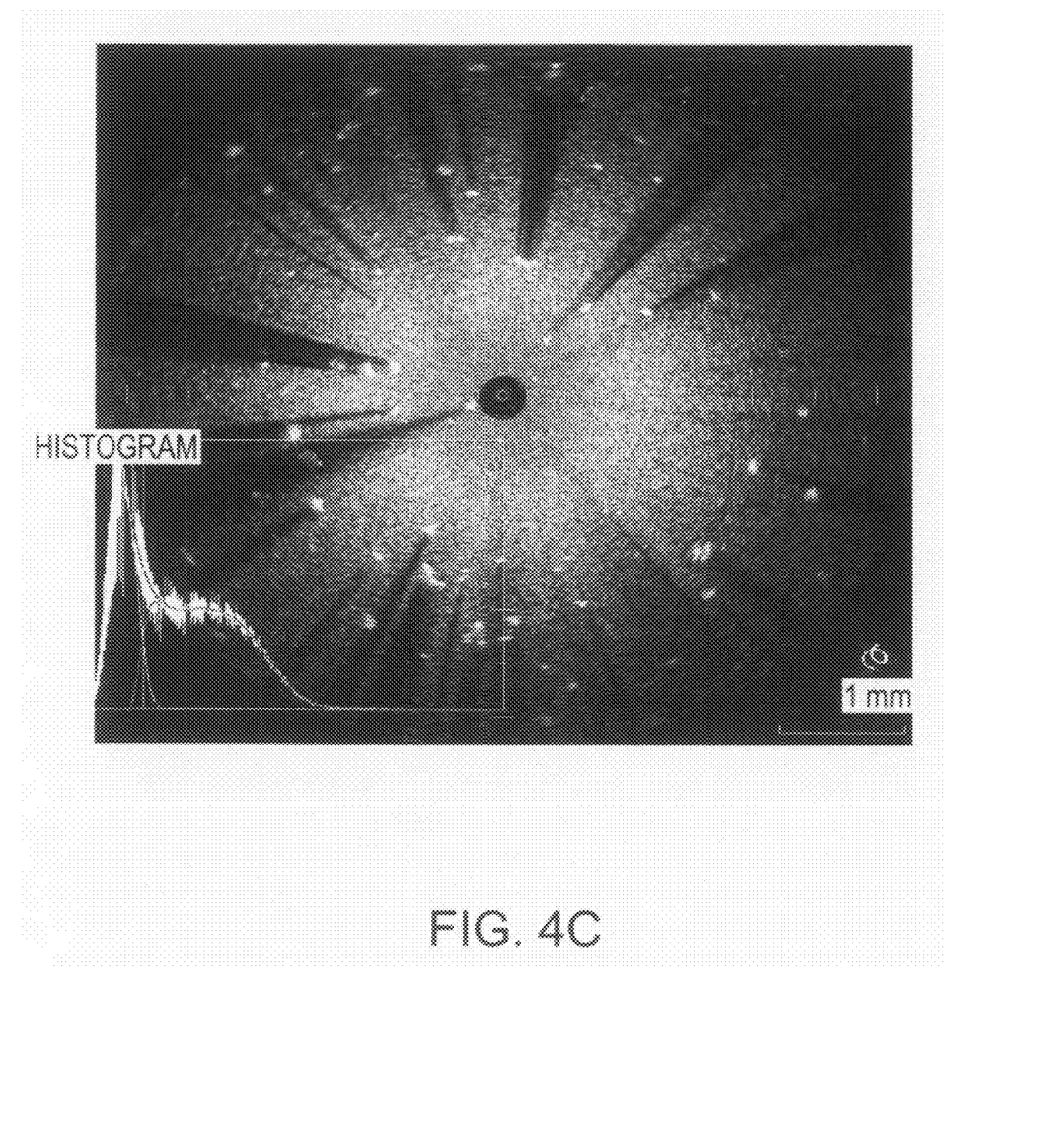
FIG. 4c depicts an OCT image in which an over-concentration of the dopant $TiO_2$ is used and the resulting clumping leads to optical shadowing.

When the zero point offset position is stable, the doped PET material produces a consistent, bright ring in the image as shown in FIG. 4a, as compared to an undoped cover FIG. 4b. When the zero point offset position is unstable, either by purposely modifying the reference path length or through stretching or compressing of the fibers during normal use, the ring is more of a spiral shape. If the concentration of $TiO_2$ particles is too high, the particles cast shadows due to clumping as shown in FIG. 4c. In one embodiment, the probe reflector element is a membrane that is capable of transmitting substantially undistorted imaging light. The term "substantially undistorted imaging light" means light that is suitable for generating an image of a sample or a sample element.

The captured data in 'raw' format is a series of radial scans, each occurring at evenly spaced angles, very much like the spokes in bicycle wheel. The raw data is stored simply in a conventional array memory format, where columns represent angles, and each row is a particular radial distance. Hence, the image of a perfect circle stored in memory would occur along the same row for each column, i.e. a straight line with zero (flat) slope. A spiral pattern is stored as a straight line with a slope, positive if the spiral is expanding, negative if the spiral is contracting.

Hence the signal from the PET material produces a line in the image that may have a flat, positive or negative slope depending on whether the optical path length is constant, increasing or decreasing. The magnitude of the slope is then proportional to the rate of change of the fiber path length in either direction due to stretching or shrinking. Because the zero point offset position is now detectable, a software algorithm can be used to isolate the PET ring by taking advantage of its bright reflection, known thickness and expected straight line representation in memory.

Figure 5:
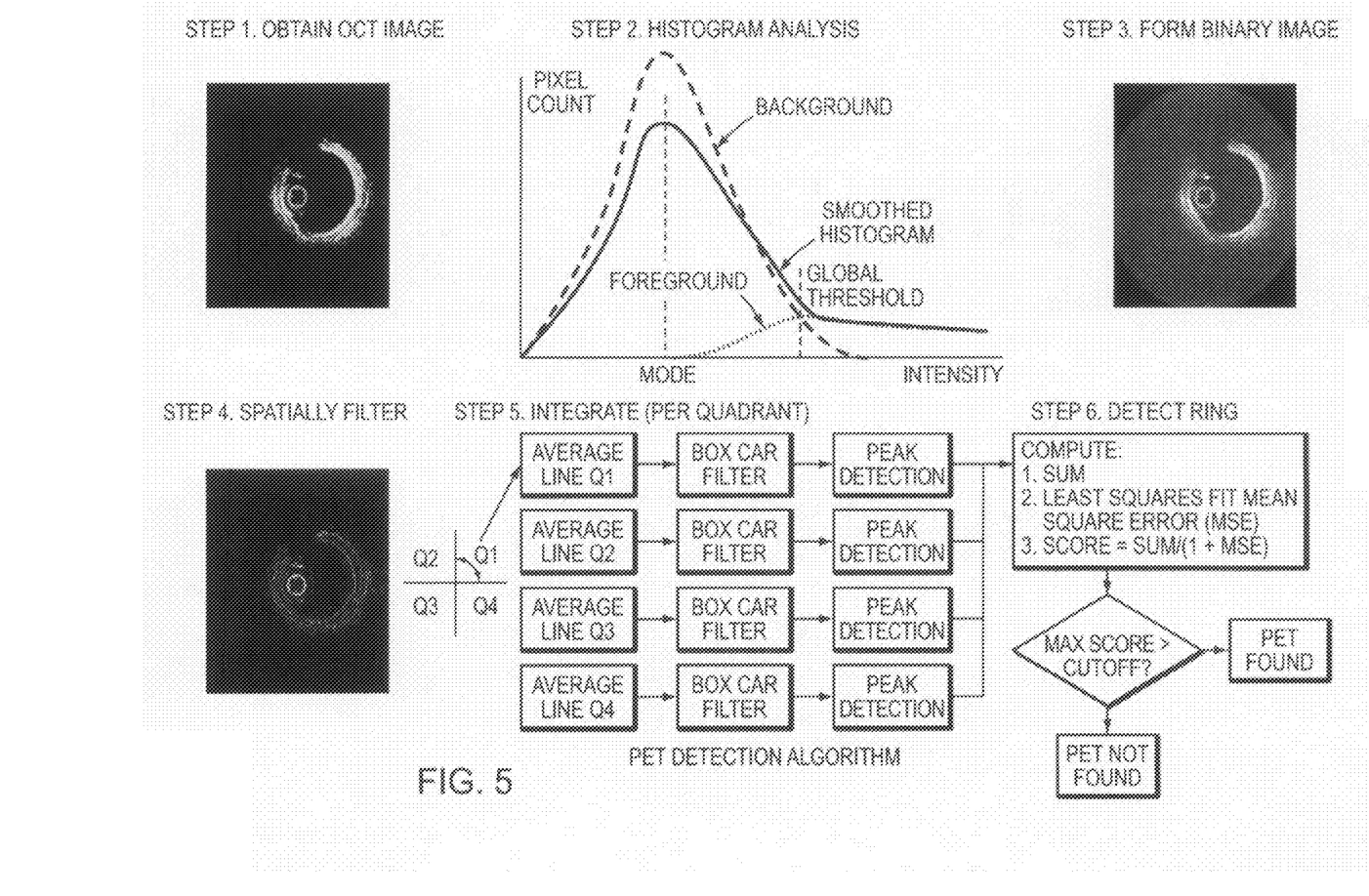
FIG. 5 is a flow chart of an embodiment of an algorithm used to detect the PET ring.

The basic steps of the algorithm are shown in FIG. 5. The OCT image is obtained (Step 1) and first analyzed on a statistical basis. This analysis calculates the number of pixels for each given intensity value. The histogram is then used to generate a "Global Threshold" value to separate the foreground tissue from background noise (Step 2). Because the image intensity will eventually fall to the background noise level, the intensity at large radial distances can be used to estimate the overall 'noise-floor' of the system. This value is then be used to produce a binary image (Step 3). Intensity values above the threshold are set to one; those below the threshold are set to zero. By analyzing the binary image and not the input OCT image, the dependence on the absolute level of the doped PET reflection is minimized.

Once the binary image is available, it is filtered with a one dimensional spatial filter (Step 4) that is designed to have peak response for a signal with thickness similar to the known PET layer thickness and adjacent black space. As shown in the figure, the influence of the tissue is greatly minimized by the spatial filter, while the PET ring is preserved.

The next step in the process (Step 5) is to average all of the scan lines in each quadrant of the filtered binary image together to produce one representative scan line per quadrant. This means, in stored memory, the columns are divided into four equal groups, and for each group, all columns are averaged together across rows to produce one representative column for each of the four 90 degree quadrants of the original image. This process serves to emphasize image content that is concentric or nearly concentric. The average is performed on a quadrant basis, as opposed to the full 360 degrees, so that the PET signal from a moving reference path (which would be spiral shaped) is not lost in the summation process. The resulting four average lines are each smoothed with a simple boxcar filter, and the brightest three peaks on each are located.

Finally, in the next step (Step 6) the peak from each quadrant's average line is selected that together produces the best ring. A recursive algorithm is used to analyze each potential group by first computing the sum of the four points and then the mean square error (MSE) of a line fitted to the points using a least squares fit algorithm. The resulting MSE is combined with the sum of the four points to form a score. This score serves to emphasize potential rings that are bright (larger sum) and flat (smaller MSE). The group with the largest score is chosen as the winner and its sum is compared to a cutoff to determine if the result is valid.

Figure 6:
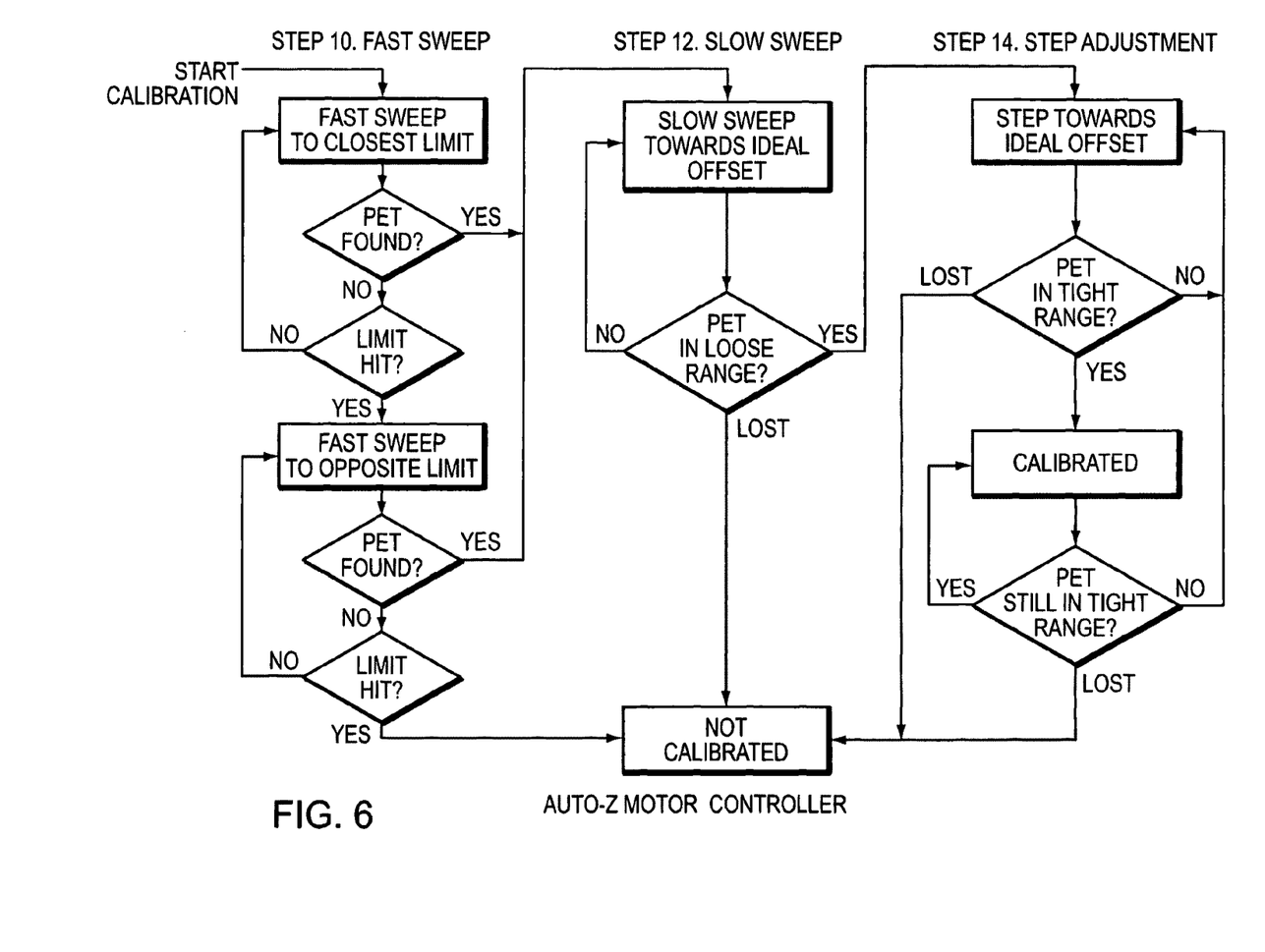
FIG. 6 is a flow chart of an embodiment of an algorithm used to set the location of the PET ring.

In operation, when a new image catheter is connected to the system, an initial coarse calibration is performed by rotating the fiber and adjusting the reference path control motor as shown in FIG. 6. The z-offset motor in the reference arm is initially swept at high speed (Step 10) between its limits while searching for the PET ring. Once the ring is found, the motor speed is slowed (Step 12) and the PET image is moved close to its desired location (zero-point, here termed the "Loose Range").

Further, once within the loose range, the motor is stepped (Step 14) until the PET image is in its final allowed range (the "Tight Range"). During live scanning the Z-Offset may drift slightly, resulting in the PET moving outside of the tight range. When this occurs, the motor is reactivated to step the PET back into the tight range. The tight range allowance is a balance set by the desired measurement accuracy and the minimization of constant z-offset motor movements During real-time imaging, the PET ring, as defined by the least squares fitted line of the winning group, is displayed at a fixed location (radius) on the screen based on the known physical location of the PET in the micro-lens assembly. The z-offset of each image frame is adjusted in or out so that the PET ring ends up at the desired location.

Figure 7:
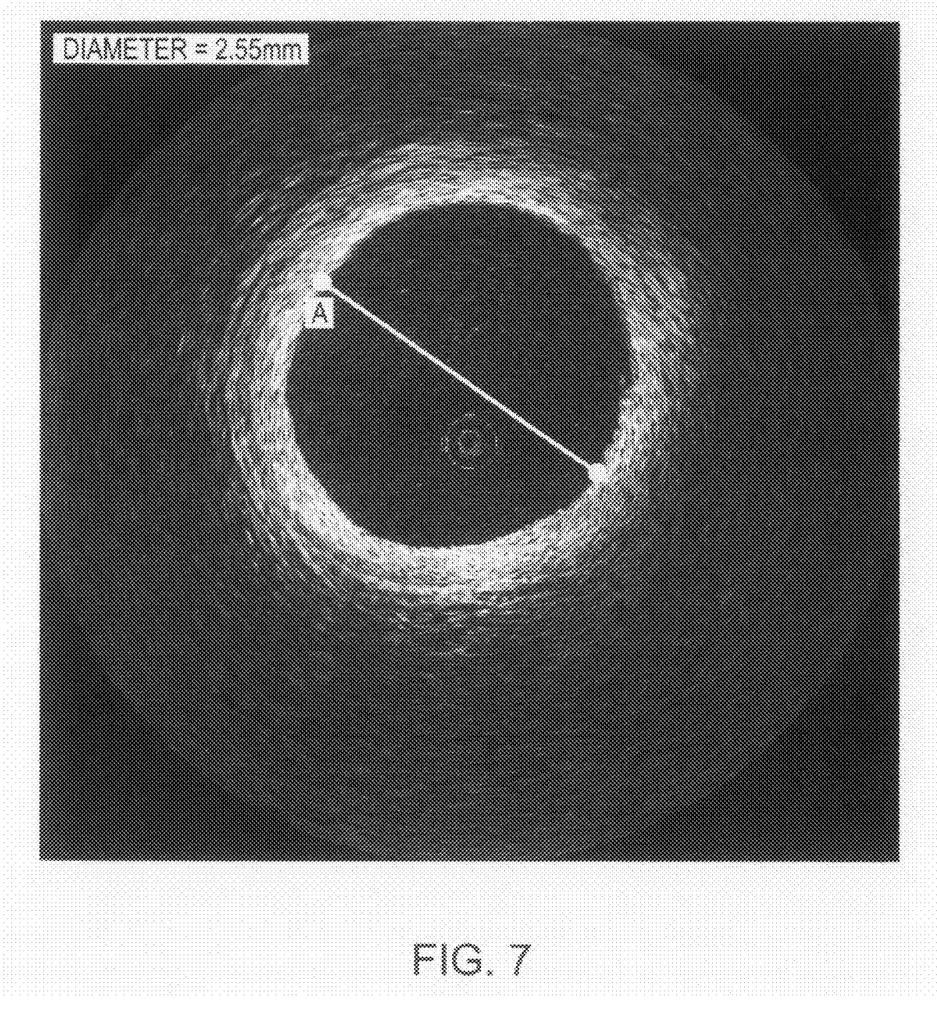
FIG. 7 depicts an image of a coronary artery made using the components in FIGS. 1 and 2 in which the zero-point offset is set correctly.
Figure 8:
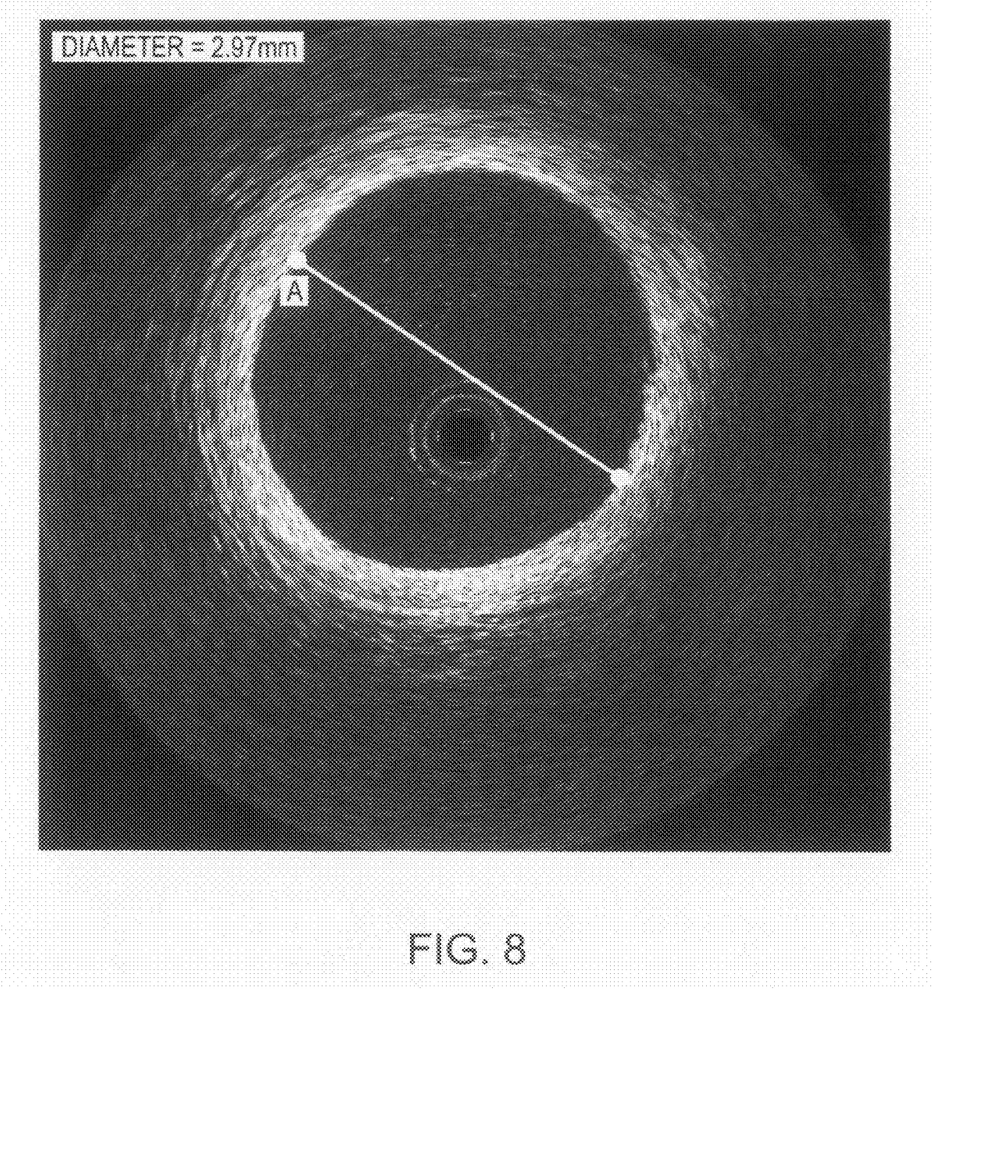
FIG. 8 depicts an image of a coronary artery made using the components in FIGS. 1 and 2 in which the zero-point offset is set incorrectly (the zero-point is too short and has been moved within the optical fiber causing the image to expand away from the center)

The final result is that the Z-Offset corrected image is displayed on the screen and stored in the saved image files, allowing correct clinical measurements to be performed in a straightforward manner. FIG. 7 is an OCT image of a coronary artery in which the z-offset is set correctly. The vessel diameter is thus correctly measured as 2.55 mm. FIG. 8 is an OCT image of a coronary artery in which the z-offset is set incorrectly such that the z-offset is positioned within the lens assembly. The vessel diameter is thus incorrectly measured as 2.97 mm.

Figure 9:
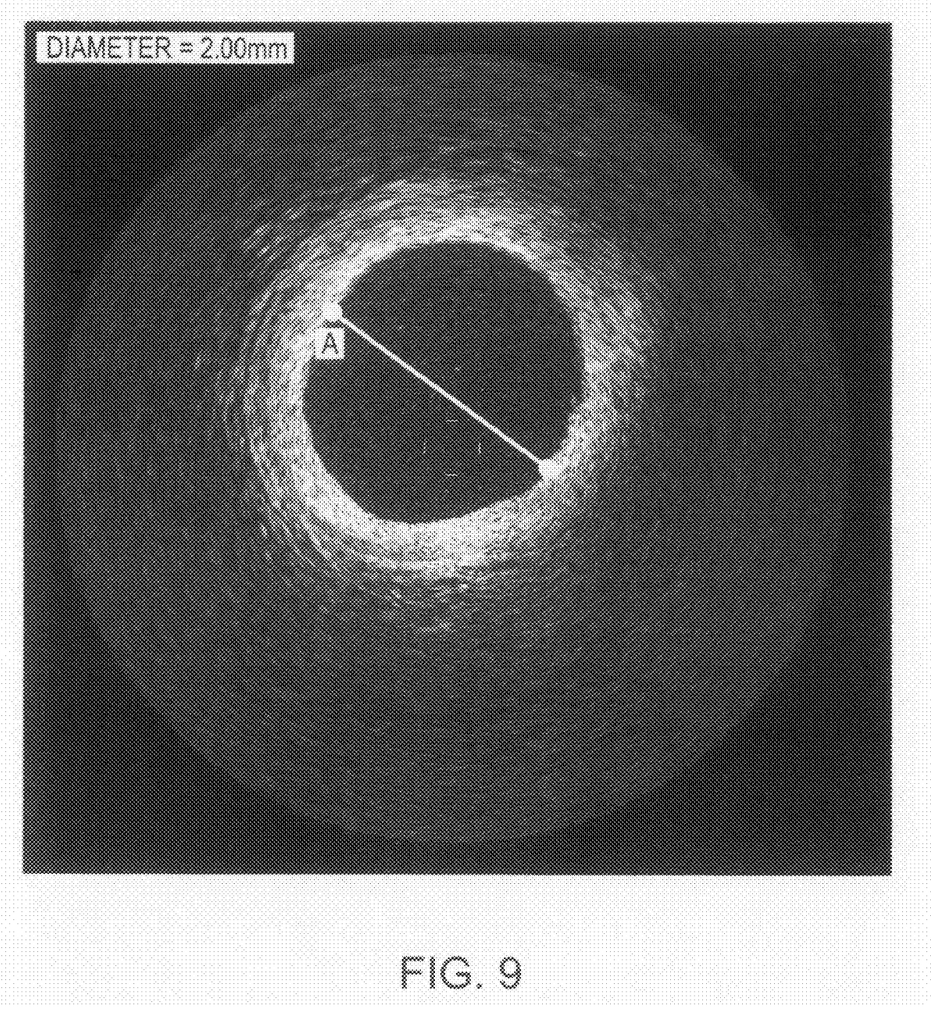
FIG. 9 depicts an image of a coronary artery made using the components in FIGS. 1 and 2 in which the zero-point offset is set incorrectly (the zero-point is too long and has moved to a point outside the fiber, causing the image to contract towards the center)

FIG. 9 is an OCT image of a coronary artery in which the z-offset is set incorrectly such that the z-offset is positioned outside the protective PET cover. The vessel diameter is thus incorrectly measured as 2.00 mm. Thus, the present invention provides a method for determining the equalization of the reference and sample paths in an OCT interferometer, to thereby provide an accurate measure of the objects of interest.

Figure 10:
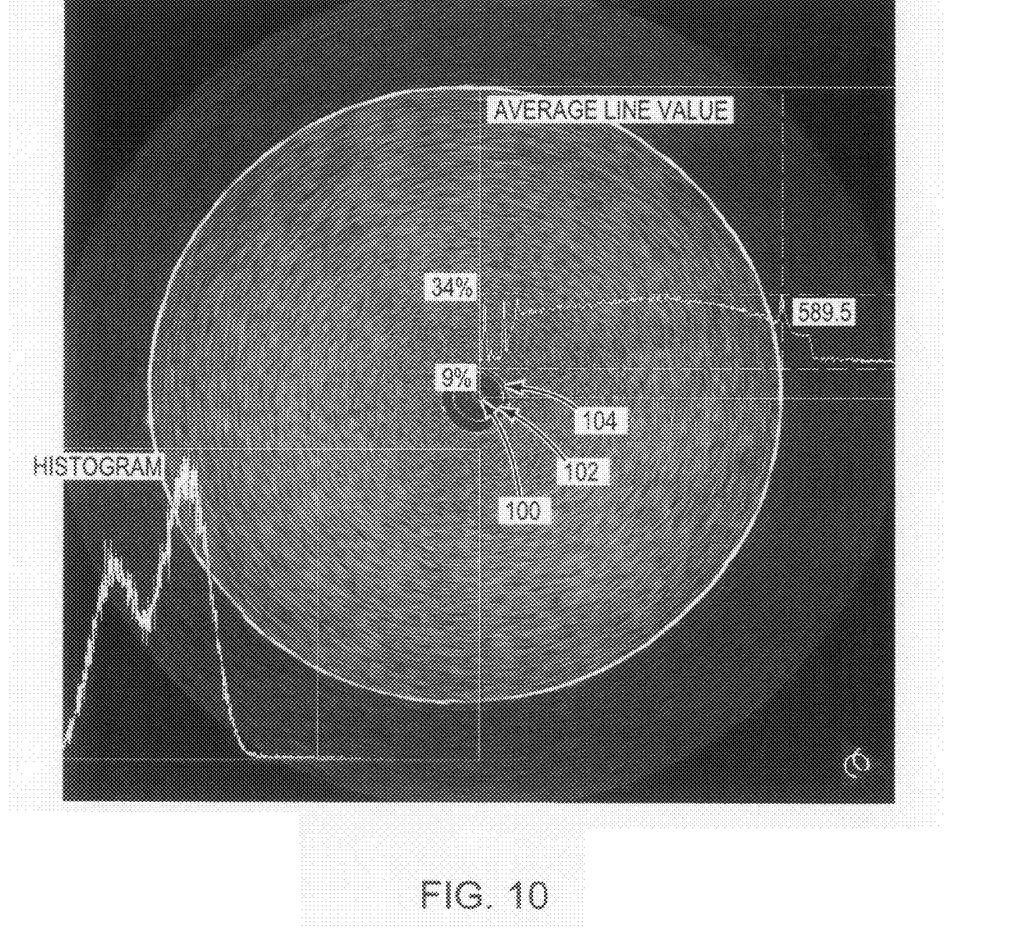
FIG. 10 depicts a magnified OCT image of a catheter center showing characteristic ring reflections according to an embodiment of the invention

FIG. 10 is another OCT image generated in accordance with aspects of the invention. Specifically, it is a magnified OCT image of a catheter center showing characteristic ring reflections arising from the micro-lens PET layer (innermost) 100 and the image wire plastic sheath (middle) 102. The outer ring 104 corresponds to the inside wall edge of the plastic tubing into which the image wire was inserted to generate the image depicted in FIG. 10. However, due to thickness of the tubing, the outer wall edge is not seen in the image.

In FIG. 10, the PET ring is generated using standard, un-doped PET. As shown, the image wire is pressed against the side of the tubing thereby causing the third outer ring 104 to be non-concentric.

It should be understood that the above-described embodiments and the following examples are given by way of illustration, not limitation. Various changes and modifications within the scope of the present invention will become apparent to those skilled in the art from the present description.

What is claimed is:

1. An optical element, the optical element comprising:
a curved cover having a first surface and a second surface, the cover forming a portion of an imaging probe, the cover comprising a polymer and a plurality of back-scattering particles for controlled optical back-scattering disposed therein such that a reference point is generated for an imaging system from the optical back-scattering, the cover allowing transmission of substantially undistorted imaging light.

2. The optical element of claim 1 wherein each of the plurality of back-scattering particles has a particle dimension, the plurality of back-scattering particles disposed within the polymer.

3. The optical element of claim 2 wherein the particle dimension is less than about 1.5 µm.

4. The optical element of claim 2 wherein the particles comprise titanium, zinc, or aluminum.

5. The optical element of claim 2 wherein the plurality of particles have a concentration of about 0.1% doping concentration by volume.

6. The optical element of claim 1 further comprising an elongate member, wherein the cover is shaped to form a sheath within which the elongate member is disposed to form a portion of a probe tip.

7. An imaging probe, the probe comprising
an elongate section having a first end and a second end;
the second end forming a probe tip capable of intra-lumen imaging and transmitting substantially undistorted imaging light,
the probe tip comprising a scattering material, the elongate section adapted to transmit light reflected by the scattering material to the first end of the elongate section,
wherein the scattering material comprises a plurality of light scattering particles.

8. The imaging probe of claim 7 wherein the elongate section is an optical fiber.

9. The imaging probe of claim 7 wherein the elongate section is a sheath and wherein the probe further comprises an optical fiber disposed within the sheath.

10. The imaging probe of claim 7 wherein the scattering particles comprise titanium and wherein the matrix comprises polyethelyne terapthalate.

11. A method of fabricating an optical element, the method comprising:
selecting a material suitable for intra-lumen use in an animal;
selecting a dopant comprising a plurality of particles suitable for dispersion in the material, the dopant adapted to scatter light in response to an optical source;
determining a dopant volume concentration such that a radial scan of a doped material generates a defined pattern;
doping the material with the selected dopant to substantially obtain the determined dopant volume concentration; and
shaping the material to faun an elongate cover for intra-lumen use in an animal, the cover allowing transmission of substantially undistorted imaging light.

12. The method of claim 11 wherein the material comprises polyethylene terepthalate.

13. The method of claim 11 wherein the dopant volume concentration is about 0.1% doping concentration by volume.

14. The method of claim 11 wherein the selected dopant comprises an oxide.

15. The method of claim 11 wherein the defined pattern is selected from the group consisting of a ring and a spiral.

16. The optical element of claim 1 wherein the controlled amount of backscatter is in an amount of light at least sufficient to generate the reference point.

17. The optical element of claim 1 wherein the imaging probe comprises an air-silica interface such that the cover preserves the air-silica interface.

18. The imaging probe of claim 7 further comprising an air-silica interface such that the probe tip preserves the air-silica interface.

19. The imaging probe of claim 7 wherein the light reflected by the scattering material is at least sufficient to generate an optical reference point suitable for calibrating an imaging system in optical communication with the imaging probe.

* * * * *